United States Patent [19]
Greenberg

[11] Patent Number: 5,328,898
[45] Date of Patent: Jul. 12, 1994

[54] FACTOR XIIIA FIBRIN BINDING FRAGMENTS

[75] Inventor: Charles S. Greenberg, Chapel Hill, N.C.

[73] Assignee: Duke University, Durham, N.C.

[21] Appl. No.: 543,116

[22] Filed: Jun. 22, 1990

[51] Int. Cl.$^5$ .................. C12N 15/54; A61K 37/52; A61K 37/00; C07K 13/00

[52] U.S. Cl. .................. 514/12; 435/172.3; 435/193; 530/350; 530/381; 930/100

[58] Field of Search .................. 530/381, 324; 514/12; 435/172.3, 193; 424/94.5; 930/240

[56] References Cited

PUBLICATIONS

Stryer, L. in *Biochemistry*, Third edition, p. 22 (1988).
Takahashi et al. (1986) Proc. Natl. Acad. Sci. U.S.A. 83:8019–8023.
Ichinose et al. (1988) Proc. Natl. Acad. Sci. U.S.A. 85:5829–5833.
Grundmann et al. (1986) Proc. Natl. Acad. Sci. U.S.A. 83:8024–8028.
K. Achyuthan et al., "Guinea Pig Liver Transglutaminase and Factor XIII A–Chains are Homologous Fibrin(ogen) Binding Proteins," in Fibrinogen 3: Biochemistry, Biological Functions, Gene Regulation and Expression, 165–69 (M. Mosesson et al. eds.) (1988).
K. Achyuthan et al., "The Binding Sites on Fibrin(ogen) for Guinea Pig Liver Transglutaminase are Similar to Those of Blood Coagulation Factor XIII," *J. Biol. Chem.* 263, No. 28, 14296 (1988).
C. Greenberg et al., "Regulation of Plasma Factor XIII Binding to Fibrin In Vitro," *Blood* 66, No. 5, 1028 (1985).
C. Greenberg et al., "Isolation of a Fibrin-Binding Fragment from Blood Coagulation Factor XIII Capable of Cross-Linking Fibrin(ogen)," *Biochem. J.* 256, 1013 (1988).
A. Ichinose et al., "Amino Acid Sequence of the a Subunit of Human Factor XIII," *Biochemistry* 25, 6900 (1986).
N. Takahashi et al., "Primary Structure of Blood Coagulation Factor XIIIa (Fibrinoligase, transglutaminase) from Human Placenta," *Proc. Natl. Acad. Sci. U.S.A.* 83, 8019 (1986).

*Primary Examiner*—Robert A. Wax
*Assistant Examiner*—Dian C. Jacobson
*Attorney, Agent, or Firm*—Bell, Seltzer, Park & Gibson

[57] ABSTRACT

Fibrin binding peptides disclosed include (a) peptides having the amino acid sequence of a human Blood Coagulation Factor XIIIA fragment (i.e., NKLIVRRGQSFYVQIDFSRPYDPRRDLF-RVEYVIGRYPQENKGTYIPVPIVSELQSGK-WGAKIVMREDR SVRLSIQSSPKCIVGKF-RMYVAVWTPYGVLRTSRNPETDTYILFNP-WCEDDAVYLDNEKEREEYVLNDIG-VIFYGEVNDIKTRSWSYGQF-R', where R' is —CONH$_2$ or —NH$_2$); (b) peptides which are fragments of the foregoing Factor XIIIA fragment and which retain the capability thereof of binding to fibrin; and (c) peptides which bind to fibrin, which have the amino acid sequence of any of the foregoing peptides, and which have additional amino acid residues attached to the N-terminal end and/or the C-terminal end thereof.

The peptides are useful for localizing blood clots in vivo, inhibiting fibrin stabilization, and promoting thrombolysis.

18 Claims, 4 Drawing Sheets

FACTOR XIIIA FIBRIN BINDING FRAGMENTS

This invention was made with Government support under Grant No. HL-38245 awarded by the National Institutes of Health. The Government may have certain rights to this invention.

BACKGROUND OF THE INVENTION

Plasma Factor XIII is an essential molecule for normal hemostasis in man. When deficiencies of Factor XIII occur or inhibitors are present they are always associated with severe, life-threatening, bleeding. This provides strong evidence that Factor XIII plays a vital role in maintaining the stability of blood clots, or the "hemostatic plug."

Plasma Factor XIII is composed of two a-chains and two b-chains which are noncovalently associated. See generally J. McDonagh, in Hemostasis and Thrombosis, 289-300 (R. Colman et al. eds. 1987). Conversion of plasma Factor XIII to its active transglutaminase form, Factor XIIIa, occurs in two steps. In the first step, thrombin cleaves a 4,000 dalton peptide from each of the a-chains with the formation of an inactive intermediate ($a_2b_2$). T. Takagi and R. Doolittle, 13 Biochemistry 750 (1974). In the next step, calcium causes the b-chains to dissociate and the active site cysteines on the thrombin-cleaved a-chains are exposed, producing Factor XIIIa ($a_2$). C. Curtis et al., 13 Biochemistry 13774 (1974).

During blood clotting, Factor XIIIa catalyzes the formation of intermolecular $\tau$-glutamyl-$\epsilon$-lysyl bonds between $\tau$-chains and $\epsilon$-chains of polymerizing fibrin monomers. Covalently modified fibrin is mechanically stronger and more resistant to lysis by plasmin when compared to noncrosslinked fibrin. See L. Shen and L. Lorand, 71 J. Clin. Invest. 1-336 (1983); Y. Sakata and N. Aoki, 65 J. Clin. Invest. 290 (1980).

The complete amino acid sequence of the a-chain was published based on protein sequence analysis and analysis of the cDNA sequence. See N. Takahashi et al., 83 Proc. Natl. Acad. Sci. USA 8019 (1986); U. Grundman et al., 83 Proc. Natl. Acad. Sci. USA 8024 (1986); A. Ichinose et al., 25 Biochemistry 6900 (1986). The entire intron and exon structure of the Factor XIII a-chain gene was recently published. A. Ichinose et al., 85 Proc. Natl. Acad. Sci. USA 5829 (1988). While little is known about how the structure of this protein relates to its function, we have found that cleavage of the activation and inactivation peptides releases a monomeric 51 kD fibrin binding peptide. See C. Greenberg et al., 256 Biochem. J. 1013 (1988).

The a-chain of plasma Factor XIII has 9 free sulfhydryl groups, one of which is in the active site of Factor XIIIa, and no disulfide bonds. The active site has sequence homology to calpains and guinea pig liver transglutaminase. See K. Ikura et al., 27 Biochemistry 2898. Tissue transglutaminases were responsible for the earliest clotting mechanisms. R. Myherman and J. Bruner-Lorand, 19 Meth. Enzymol. 765 (1970). Guinea pig liver transglutaminase is one of the more extensively studied tissue transglutaminases. Guinea pig liver transglutaminase was recently cloned and was found to share several homologous domains with Factor XIII a-chains. See K. Ikura et al., 27 Biochemistry 2898 (1988). We found that the two proteins shared homologous fibrin binding domains. See K. Achyuthan et al., J. Biol. Chem. 263, 14296 (1988). We detected six homologous regions when we compared the sequence of Factor XIII and the guinea pig liver transglutaminase See K. Achyuthan et al., in Fibrinogen 3: Biochemistry, Biological Functions, Gene Regulation and Expression, 165-69 (M. Mosesson et al. eds. 1988).

The present invention is based on our ongoing research into the structure and function of Factor XIIIa.

SUMMARY OF THE INVENTION

Figure 1A:
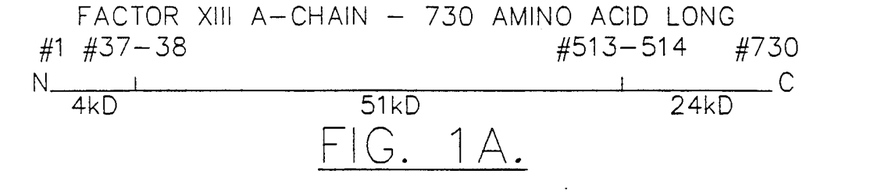
FIGS. 1A-1C illustrates the human plasma Factor XIII A-Chain (FIG. 1A), the fibrin binding domain of the Factor XIII A-Chain (FIG. 1B), and a Factor XIIIa fragment of the present invention (FIG. 1C).
Figure 1B:
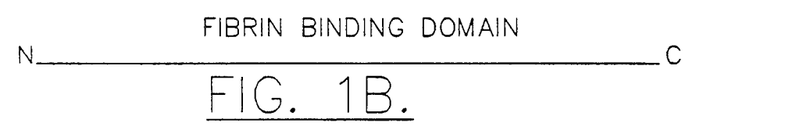
Figure 1C:
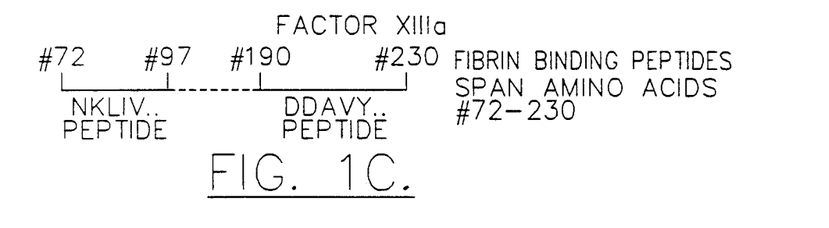

A first aspect of the present invention is a fibrin-binding peptide having the amino acid sequence of the Blood Coagulation Factor XIIIA fragment shown in FIG. 1C.

A second aspect of the present invention is fibrin-binding peptides which are fragments of the Factor XIIIA fragment shown in FIG. 1C and which retain the capability of the fragment of FIG. 1C of binding to fibrin.

A third aspect of the present invention is peptides which bind to fibrin, which have the amino acid sequence of any of the foregoing peptides, and which have additional amino acid residues attached to the N-terminal end and/or the C-terminal end. The number of additional amino acids may, for example, be up to about 10, but this number is not critical so long as the peptide does not gain the activity of the native enzyme (i.e., the ability to cross-link fibrin) or, through folding, lose the capability of binding to fibrin.

These peptides are useful for localizing blood clots in vivo, inhibiting fibrin stabilization, and promoting thrombolysis.

DETAILED DESCRIPTION OF THE INVENTION

Amino acid residues are identified by either a three letter or single letter abbreviation herein in the following manner:

| | |
|---|---|
| Ala; A = Alanine | Leu; L = Leucine |
| Arg; R = Arginine | Lys; K = Lysine |
| Asn; N = Asparagine | Met; M = Methionine |
| Asp; D = Aspartic acid | Phe; F = Phenylalanine |
| Cys; C = Cysteine | Pro; P = Proline |
| Gln; Q = Glutamine | Ser; S = Serine |

| | |
|---|---|
| Glu; E = Glutamic acid | Thr; T = Threonine |
| Gly; G = Glycine | Trp; W = Tryptophan |
| His; H = Histidine | Tyr; Y = Tyrosine |
| Ile; I = Isoleucine | Val; V = Valine |

FIG. 1 illustrates an embodiment of the present invention in relation to the prior art. The human plasma Factor XIII A-chain is shown as FIG. 1A. This chain and its sequence is known. See A. Ichinose et al., Biochemistry 25, 6900-06 (1986). A 51 Kd fragment of the Factor XIII A-chain which binds to fibrin and is itself capable of cross-linking fibrin(ogen), is shown as part of FIG. 1A. The 51 Kd fragment is also known. See C. Greenberg et al., Biochem. J. 256, 1013-19 (1988). The active enzyme, Factor XIIIa, is shown as FIG. 1B. Finally, a peptide of the present invention is shown as FIG. 1C. The complete amino acid sequence of the peptide of FIG. 1C is given below. Note that the peptide of FIG. 1C incorporates two separate fibrin binding regions.

A peptide of the invention may be produced by chemical synthesis in accordance with known procedures. In general, the peptide is built up either from the N-terminus or, more typically, the C-terminus using either single amino acids or preformed peptides containing two or more amino acid residues. Particular techniques for synthesizing peptides include (a) classical methods in which peptides of increasing size are isolated before each amino acid or preformed peptide addition, and (b) solid phase peptide synthesis in which the peptide is built up attached to a resin such as a Merrifield resin. In these synthetic procedures, groups on the amino acids will generally be in protected form using standard protecting groups such as t-butoxycarbonyl. If necessary, these protecting groups are cleaved once the synthesis is complete. Other modifications may be introduced during or after the synthesis of the peptide.

Examples of peptides of the present invention include, but are not limited to, the following:

(A) NKLIVRRGQSFYVQIDFSRPYDPRRDLF-RVEYVIGRYPQ ENKGTYIPVPIVSELQSGK-WGAKIVMREDRSVRLSIQSSPKCIVGKF-RMYVAVW TPYGVLRTSRNPETDTYILFNP-WCEDDAVYLDNEKEREEYVLNDIG-VIFYGEVNDIKTRSWSYGQF-R', where R' is —CONH₂ or —NH₂ (the complete sequence of the peptide of FIG. 1C discussed above);

(B) DDAVYLDNEKEREEYVLNDIG-VIFYGEVNDIKTRSWSYGQFR', where R' is —CONH₂ or —NH₂ (a fragment of peptide A hereafter referred to as the "DDAVY. . . peptide"); and (C) NKLIVRRGQSFYVQIDFSRPYDPRRD-R', where R' is —CONH₂ or —NH₂ (a fragment of peptide A hereafter referred to as the "NKLIV. . . peptide"). Whether R' is —CONH₂ (the amide) or —NH₂ (the amine) will depend on the particular method of synthesizing the peptide chosen.

The NKLIV. . . peptide and the DDAVY. . . peptide represent two separate fibrin binding regions found in the peptide of FIG. 1C above. Thus, other fragments of FIG. 1C can be synthesized which include the sequence, of: DDAVYLDNEKEREEYVLNDIG-VIFYGEVNDIKTRSWSYGQF, and which are useful for practicing the present invention. Likewise, other fragments of FIG. 1C can be synthesized which include the sequence, of: NKLIVRRGQSFYVQIDFSR-PYDPRRD. Additional amino acids may, as noted above, optionally be joined to the N-terminus and/or the C-terminus of either of these sequences.

Peptides which are fragments of the foregoing, and which retain the capability of binding to fibrin, are also an aspect of the present invention. The capability of a peptide for binding to fibrin may be routinely tested by a variety of means, several of which are disclosed in the examples set forth below.

Those skilled in the art will appreciate that minor deletions or substitutions may be made to the amino acid sequences of peptides of the present invention without unduly adversely affecting the ability of such peptides to bind to fibrin. Thus, peptides containing such deletions or substitutions are a further aspect of the present invention.

Peptides of the present invention may be covalently joined to a suitable detectable group, such as biotin, radiolabels (e.g., $^{125}$I and $^{131}$I) or fluorescent labels (e.g., fluorescein), and the labelled peptide then used to identify blood clots in vivo.

Peptides of the present invention may be covalently joined to other compounds, such as a protease capable of degrading fibrin, to produce a conjugate capable of binding to a blood clot. Joining of the peptides with such other compounds may be carried out through either synthetic chemical or recombinant DNA procedures. A covalent conjugate produced through recombinant DNA procedures is referred to herein as a "fusion protein." Other compounds suitable for conjugation to the peptides disclosed herein include tissue plasminogen activator, urokinase, streptokinase, and plasmin. Examples of such other compounds include, but are not limited to, those disclosed in U.S. Pat. Nos. 4,916,071; 4,892,826; 4,853,330; 4,766,075; 4,752,063; 4,558,010; and 4,370,407. The disclosures of these and all other patent references cited herein are to be incorporated herein by reference.

Peptides and fusion proteins of the present invention may, as noted above, be produced through recombinant DNA procedures. Nucleotide sequences for DNA sequences which code for peptides or fusion proteins of the present invention (useful as intermediates for making the same) can be determined with any table setting forth the genetic code. See, e.g., R. Old and S. Primrose, Principles of Gene Manipulation, 346 (3d Ed. 1985).

The peptides and fusion proteins disclosed herein can be prepared in the form of their pharmaceutically acceptable salts. Pharmaceutically acceptable salts are salts that retain the desired biological activity of the parent compound and do not impart undesired toxicological effects. Examples of such salts are (a) acid addition salts formed with inorganic acids, for example hydrochloric acid, hydrobromic acid, sulfuric acid, phosphoric acid, nitric acid and the like; and salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; and (b) salts formed from elemental anions such as chlorine, bromine, and iodine.

The peptides and fusion proteins described herein can be combined with an inert pharmaceutical carrier to provide a pharmaceutical composition for enteral or parenteral administration. The compounds described above being the active ingredient in these compositions, they should be included in an amount effective to accomplish the intended treatment. For the preparation of these compositions, use can be made of pharmaceutical carriers adapted for all conventional forms of administration, for example, tablets, capsules, dragees, syrups, solutions, suspensions and the like. As injection medium, it is preferred to use water which contains the additives usual in the case of injection solutions, such as stabilizing agents, solubilizing agents and/or buffers. Additives of this kind include, for example, human serum albumin and synthetic analogs thereof, tartrate and citrate buffers, ethanol, complex formers (such as ethylenediamine-tetraacetic acid and the non-toxic salts thereof) and high molecular weight polymers (such as liquid polyethylene oxide) for viscosity regulation. Liquid carrier materials for injection solutions must be sterile and are preferably placed into ampules. Solid carrier materials include, for example, starch, lactose, mannitol, methylcellulose, talc, highly dispersed silicic acids, high molecular weight fatty acids (such as stearic acid), gelatine, agar-agar, calcium phosphate, magnesium stearate, animal and vegetable fats and solid high molecular weight polymers (such as polyethylene glycols). Compositions suitable for oral administration can, if desired, contain flavoring and/or sweetening agents.

A method of inhibiting fibrin stabilization in a subject in need of such treatment comprises administering a peptide of the present invention to the subject in an amount effective to inhibit fibrin stabilization.

A method of promoting thrombolysis in a subject in need of such treatment comprises administering a peptide of the present invention to the subject in an amount effective to promote thrombolysis.

A method of localizing blood clots in a subject suspected of containing the same comprises administering to such a subject a labelled peptide of the present invention in an amount effective to bind a detectable quantity of the labelled peptide to the blood clot.

Any suitable route of administration may be employed in carrying out the methods of present invention, including administration by intraveneous injection, intraarterial injection, intraperitoneal injection, intramuscular injection, and subcutaneous injection. Preferred routes of administration are by intraveneous and intraarterial injection.

Subjects to be treated by the methods disclosed herein are preferably mammalian subjects, such as human, cat, dog, and horse subjects. Thus, the present invention has both medical and veterinary applications. Dosage of peptide administered will vary depending upon subject species, subject condition, the nature of the condition being addressed and the route of administration. Dosage may be from about 10 micrograms to about 2.0 milligrams of peptide per Kilogram of subject body weight when given intravenously or intraarterially.

The Examples which follow are illustrative of specific embodiments of the invention, and various uses thereof. They are set forth for explanatory purposes only, and are not to be taken as limiting the invention.

EXAMPLE 1

Synthesis of Peptides

The synthetic peptides DDAVY. . . and NKLIV. . . were synthesized by Multiple Peptide Systems, Inc. Synthetic procedures employed the standard t-butyloxycarbonyl chemistry. Deprotection was done with 55% trifluoroacetic acid in methylene chloride followed by neutralization with diisopropylethylamine. Coupling was carried out using 0.1M amino acid solution in dicyclohexylcarbodiimide. The lyophilized peptides were stored at −20° C. until use. The peptides had the following sequences:

(A)                 DDAVYLDNEKEREEYVLNDIG-VIFYGEVNDIKTRSWSYGQF-amide; and
(B) NKLIVRRGQSFYVQIDFSRPYDPRRD-amide.

EXAMPLE 2

Purification of the DDAVY. . . Peptide

The peptide DDAVY. . . was dissolved in either water or 0.2M Tris, 0.15M NaCl (TBS), pH 7.4. The peptide suspension was then microfuged and the clear supernatant was injected on to a Vydac C-18 reverse phase HPLC column and eluted with a linear gradient of 0.1% trifluoroacetic acid in 30% water and 70% acetonitrile (gradient=5% to 100%). Purified DDAVY. . . peptide eluted at 22.0 to 22.5 minutes. The purified peptide peak from 34 HPLC runs was pooled and evaporated using a Speed Vac. The residue was dissolved in water and the identity of the material was verified by amino acid sequencing by automated Edman degradation in an Applied Biosystems (Foster City, Calif.) 470 A gas/liquid-phase sequencer with the O2RPTH program and chemicals supplied by the manufacturer. The phenylthiohydantoin derivatives were analyzed immediately after each cycle by reverse-phase HPLC on a Hewlett-Packard 1090 liquid chromatograph with an ABI PTH-C-18, 2.1 mm×220 mm cartridge and the conditions recommended by the manufacturer.

EXAMPLE 3

Radioiodination of the DDAVY. . . Peptide

The HPLC purified DDAVY. . . peptide prepared in Example 2 above was radioiodinated using Iodogen beads (Pierce) and 1.0 mCi of $^{125}$INa (Amersham). Radiolabeled peptide was separated from free iodine by filtering over a Sephadex G-10 column.

EXAMPLE 4

Separation of N-Terminal and C-Terminal Derived Peptides from the DDAVY. . . Peptide Sequence That Do Not Bind Fibrin By reverse phase HPLC, peptides containing portions of the N- and C-terminal amino acid sequences of the DDAVY. . . peptide were separated from the full length DDAVY. . . peptide. Radiolabeled peptides with the following sequences did not bind to fibrin and could be detected in the unbound material when analyzed by reverse phase HPLC: 1) KTRSWSYGQF and 2) GEVNDIKTRSWSYGQF. Only the full length 41-mer DDAVY. . . peptide bound to fibrin.

EXAMPLE 5

Fibrin Binding Assay

Binding of radiolabeled DDAVY. . . peptide prepared in accordance with Example 3 above was conducted in the presence of the following proteins: human albumin (Kabi), bovine serum albumin (BSA), hemoglobin, and cytochrome C. Fibrin binding was performed by incubating 0.5 mg/mL fibrinogen, 0.1% Triton X-100, 0.15M NaCl, 0.1M Tris, pH 7.4 (TBS), 10 mM CaCl$_2$, and $^{125}$I-labeled DDAVY. . . peptide and the mixture was clotted by the addition of 10 U/mL of thrombin. After 10 minutes at 37° C., the fibrin was compressed by centrifugation (10–12,000 rpm for 10 minutes), washed thrice with TBS and the bound radioactivity was quantitated using a gamma Counter. Proteins were included in the binding mixture at these concentrations: hemoglobin (100 micromolar); human albumin (Kabi) (100 micromolar); and cytochrome C (500 micromolar). Fibrin concentration was approximately 1.0 micromolar. Under these conditions, only 1.7% of free $^{125}$I-Na was found to be trapped nonspecifically by the fibrin.

EXAMPLE 6

Binding of DDAVY. . . Peptide in the Presence of Factor XIIIa-Chains

Purified recombinant platelet Factor XIII A-chains were used to inhibit the binding of DDAVY. . . peptide to fibrin. At a concentration of 0.4 mg/mL fibrinogen, 2.0 mg/mL of recombinant platelet Factor XIII inhibited the binding of DDAVY. . . peptide to fibrin by 76%. In another experiment, purified placental Factor XIII A-chains were used to inhibit DDAVY. . . peptide binding to fibrin. Binding was conducted in the presence of 1.0 mg/mL fibrinogen, 5 nanomoles of placental Factor XIII and approximately 0.05 nanomoles of the DDAVY. . . peptide. Under these conditions, the binding of the peptide to fibrin was inhibited by nearly 44%.

EXAMPLE 7

Effect of Unlabeled DDAVY. . . Peptide on $^{125}$I-DDAVY. . . Peptide Binding to Fibrin Binding of radiolabeled DDAVY. . . peptide (approximately 52 pmoles) was mixed with unlabeled DDAVY. . . peptide (approximately 34 nanomoles; =660-fold molar excess over radiolabeled peptide) and the mixture was bound to 0.1 mg/mL fibrin. Under these conditions, the binding of radiolabeled peptide was inhibited by nearly 83%. In another experiment, when radiolabeled peptide (2.0 micrograms/mL) was mixed with unlabeled DDAVY. . . peptide (1.0 mg/mL) and the mixture was bound to fibrin (0.2 mg/mL), binding of the radiolabeled peptide to fibrin was inhibited completely. In these experiments and in the experiments conducted in the presence of XIII, binding values were corrected for nonspecific binding observed in the absence of thrombin and/or in the presence of XIII or unlabeled DDAVY. . . peptide alone.

EXAMPLE 8

Figure 2:
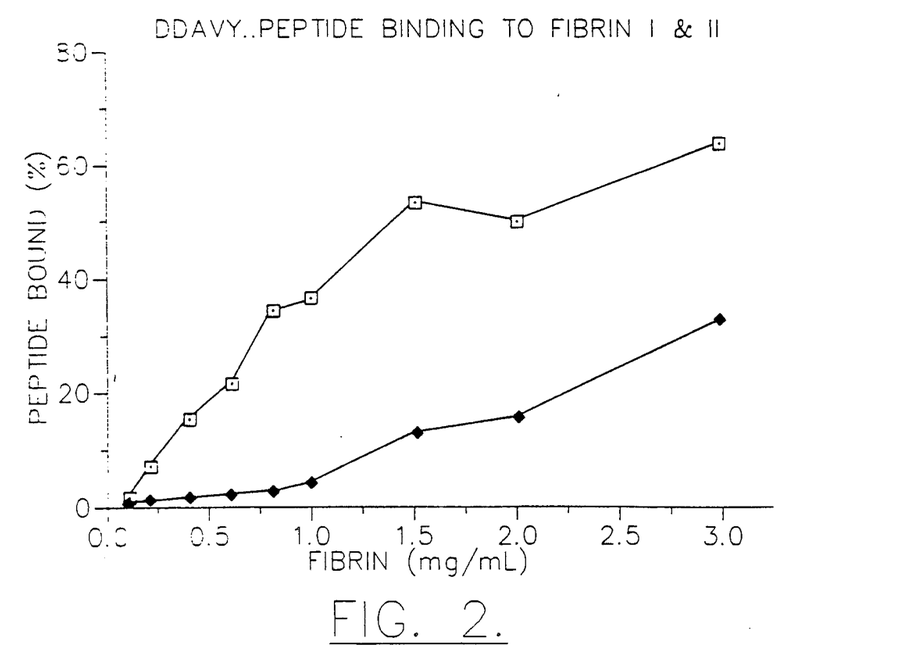
FIG. 2 illustrates the effect of fibrin concentration on the binding of $^{125}$I-DDAVY... peptide to fibrin I and II.

Effect of Fibrin Concentration on the Binding of $^{125}$I-DDAVY. . . peptide to Fibrin I and II The effect of fibrin concentration on the binding of $^{125}$I-DDAVY. . . peptide to fibrin I and II is shown in FIG. 2. Increasing concentrations of fibrinogen was incubated with $^{125}$I-DDAVY. . . peptide (2–3 ×10$^5$ cpm) in 0.1M Tris, pH 7.4 containing 0.15M NaCl (=Tris-buffered saline, TBS). The reaction mixture also contained 10mMCaCl$_2$, 0.1% (v/v) Tween-20 and 0.1% (w/v) bovine serum albumin. Binding was initiated by the addition of either thrombin (10 U/mL) (open squares) (Fibrin II) or atroxin (0.05 micrograms) (closed squares) (Fibrin I) and the mixture incubated at 37° C. for 10 minutes. Then the fibrin was compressed by centrifugation (10,000 rpm, 10 minutes at room temperature, 25° C. approximately). The supernatant was removed and discarded. The fibrin pellet was washed thrice by resuspension in TBS followed by centrifugation. Then, the radioactivity associated with the fibrin was measured using a gamma-Counter.

EXAMPLE 9

Figure 3:
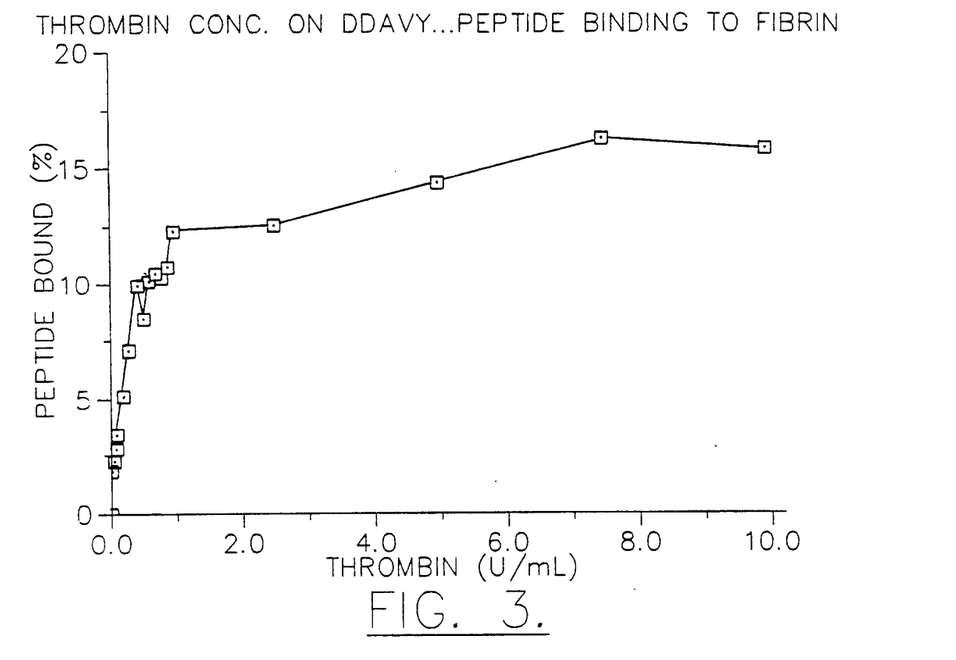
FIG. 3 illustrates the effect of thrombin concentration on the binding of $^{125}$I-DDAVY... peptide to fibrin II.

Effect of Thrombin Concentration on the Binding of $^{125}$I-DDAVY... Peptide to Fibrin II The effect of thrombin concentration on the binding of $^{125}$I-DDAVY. . . peptide to fibrin II is shown in FIG. 3. The binding experiment was conducted in the presence of increasing concentrations of thrombin under conditions essentially the same as described in Example 8. Fibrinogen concentration was 0.4 mg/mL.

EXAMPLE 10

Figure 4:
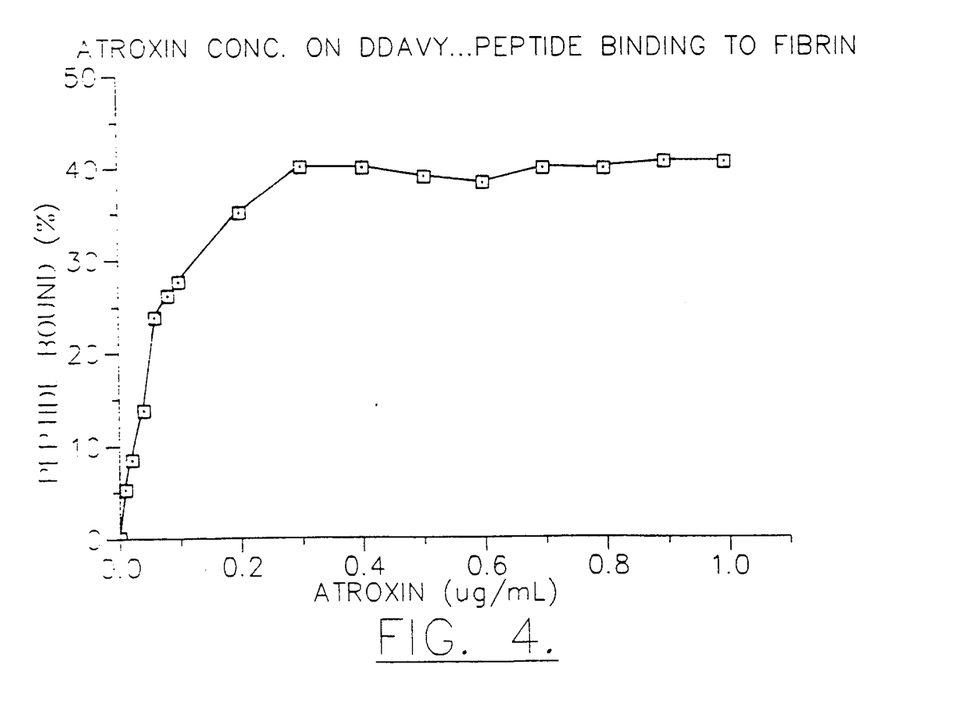
FIG. 4 illustrates the effect of Atroxin concentration on the binding of $^{125}$-DDAVY... peptide to fibrin I.

Effect of Atroxin Concentration on the Binding of $^{125}$I-DDAVY. . . Peptide to Fibrin I The effect of atroxin concentration on the binding of $^{125}$I-DDAVY. . . peptide to fibrin I is shown in FIG. 4. This binding experiment was conducted in the presence of increasing concentrations of atroxin under experimental conditions essentially the same as described in Example 8. Fibrinogen concentration was 2.0 mg/mL and DDAVY. . . peptide had a radioactivity of 2×10$^5$ cpm.

EXAMPLE 11

Time Course of DDAVY. . . Peptide Binding to Fibrin II

Figure 5:
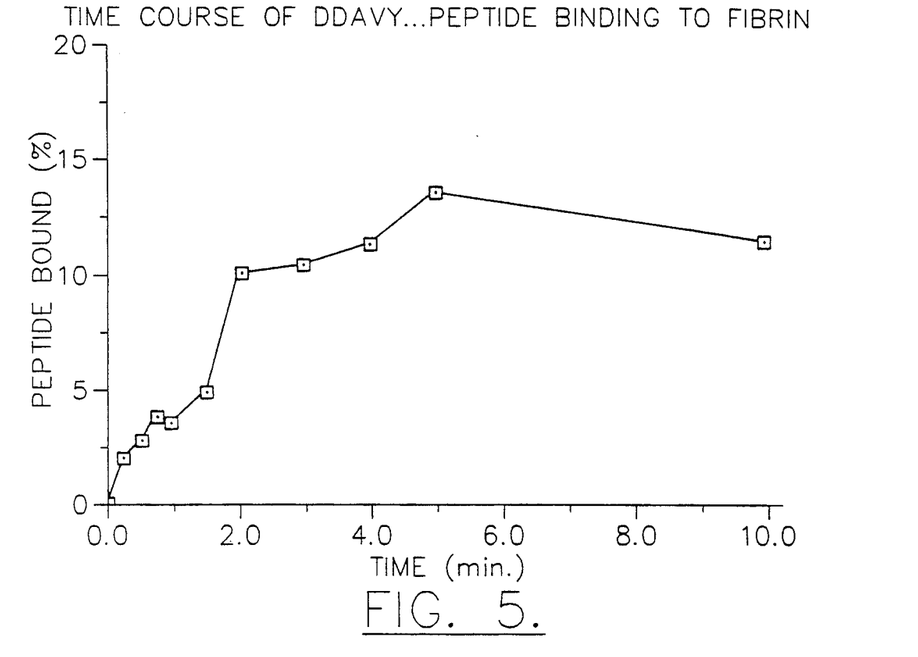
FIG. 5 illustrates the time course of DDAVY... peptide binding to fibrin II.

The time course of DDAVY. . . peptide binding to fibrin II is shown in FIG. 5. This binding experiment was conducted essentially as described in Example 8. Fibrinogen concentration in the binding mixture was 0.4 mg/mL and $^{125}$I-DDAVY. . . peptide was used at a concentration of 1.2×10$^5$ cpm. The binding reaction was terminated at the indicated time periods and then the fibrin-associated radioactivity was measured.

EXAMPLE 12

Figure 6:
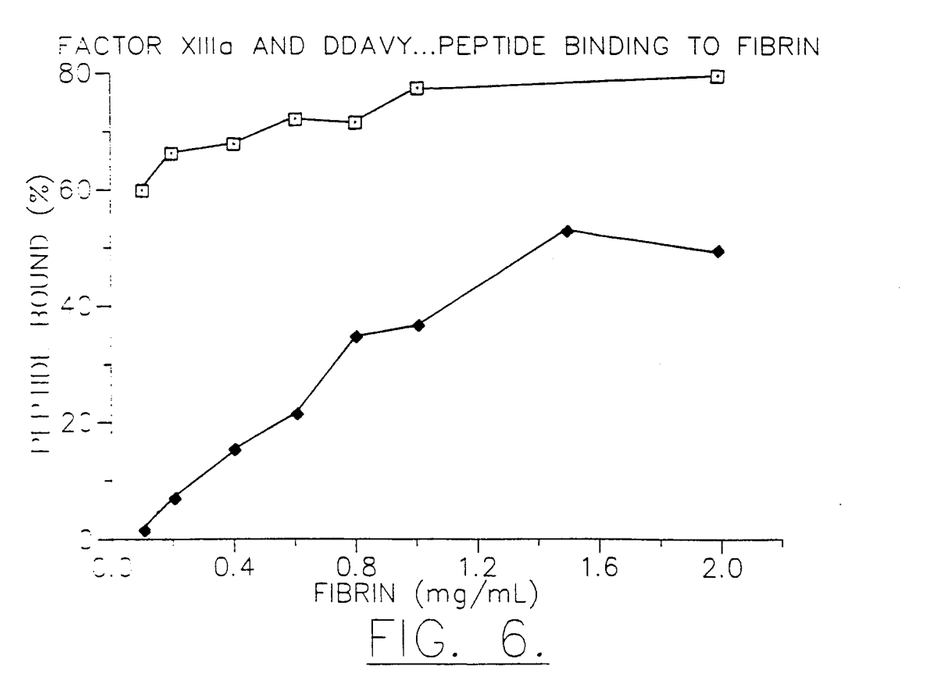
FIG. 6 illustrates a comparison of the affinities of purified, recombinant, Platelet Factor XIII A-Chains and DDAVY... peptide For fibrin II.

Comparison of the Affinities of Purified, Recombinant, Platelet Factor XIIIA-Chains and DDAVY. . . Peptide For Fibrin II A comparison of the affinities of purified, recombinant, platelet factor XIII A-chains and DDAVY. . . Peptide For Fibrin II is shown in FIG. 6. The open squares represent DDAVY. . . Peptide binding and the closed diamonds represent Factor XIII A-chain binding. This binding experiment was conducted essentially as described in connection with Example 8. Increasing concentrations of fibrinogen was incubated with purified, radiolabeled, recombinant platelet Factor XIII A-chains (1.6×10$^5$ cpm) or purified, radiolabeled DDAVY. . . peptide (2×10$^5$ cpm) and the mixture was clotted by the addition of 10 U/mL of thrombin. Clot bound radioactivity was measured using a gamma-Counter.

EXAMPLE 13

Figure 7:
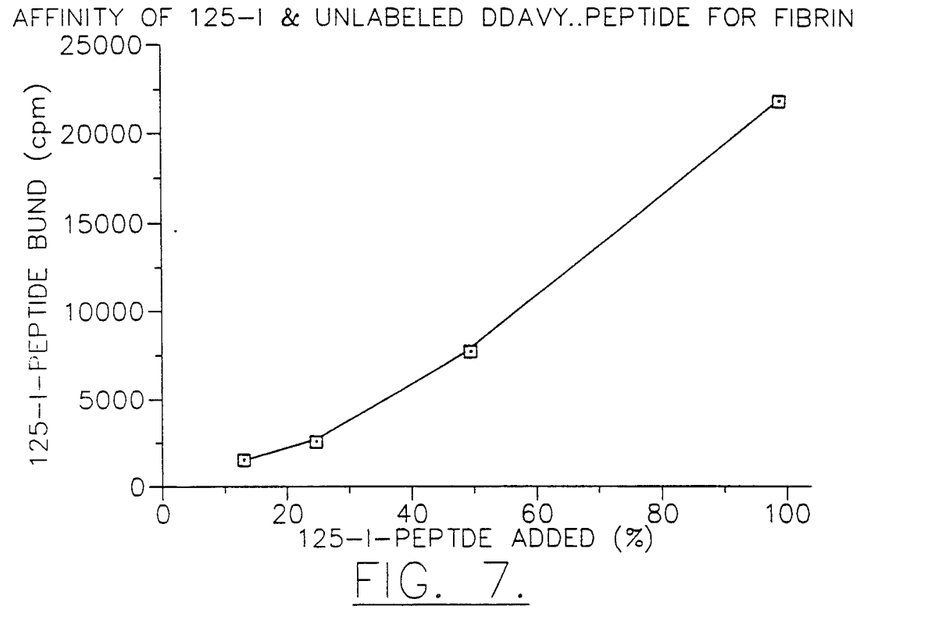
FIG. 7 illustrates a comparison of the affinities of $^{125}$I-labeled DDAVY... peptide and unlabeled DDAVY... peptide for fibrin II.

Comparison of the Affinities of $^{125}$I-labeled DDAVY. . . peptide and Unlabeled DDAVY. . . peptide for Fibrin II A comparison of the affinities of $^{125}$I-labeled DDAVY. . . peptide and unlabeled DDAVY. . . peptide for fibrin II is shown in FIG. 7. This binding experiment was conducted by adding increasing amounts of radiolabeled DDAVY... peptide to unlabeled DDAVY... peptide. However, the total amount of DDAVY... peptide (radiolabeled+unlabeled) in the incubation mixture was kept constant. All other experimental conditions were as described in Example 8 above. The amount (cpm) of peptide bound to fibrin was quantified using a gamma-Counter. The "r" value was 0.987.

EXAMPLE 14

Effect of DDAVY... Peptide and NKLIV... Peptide on Factor XIIIa-Catalyzed Crosslinking of Fibrin II This example illustrates the effect of DDAVY... peptide and NKLIV... peptide on fibrin crosslinking by Factor XIIIa. Purified human fibrinogen (0.27 mg/mL) was mixed with increasing concentrations (56 micromolar to 280 micromolar) of the DDAVY... peptide and incubated for 15 minutes at 37° C. Then, calcium chloride was added in 0.1M Tris, pH7.4 containing 0.15M NaCl (Tris-buffered saline, TBS) to make the final calcium concentration equal 10 mM. The mixture was then clotted by the addition of 10 U/mL thrombin. Thrombin also served to activate the catalytic amounts of Factor XIII present in the fibrinogen preparation. The mixture was incubated for an additional 15 minutes at 37° C. and then solubilized in SDS-PAGE buffer containing 5% sodium dodecylsulfate (SDS), 4M urea, 10mM Tris, pH7.4, 1.0 mM ethylenediaminetetraacetic acid (EDTA), 1% 2-mercaptoethanol, and 0.001% bromophenol blue. The mixture was boiled for 5 minutes, cooled, and then separated by electrophoresis on a 4-15% linear gradient polyacrylamide gel (SDS-polyacrylamide gel electrophoresis, SDS-PAGE). After electrophoresis, the gel was stained using Coomassie Brilliant Blue and destained. Control incubations were conducted simultaneously that contained no peptide. Inhibition of fibrin crosslinking could be detected around 112 micromolar and nearly 50% inhibition was observed at 280 micromolar concentrations of the DDAVY... peptide.

The reaction was also conducted as described for the DDAVY... peptide, except that NKLIV... peptide was substituted for the DDAVY... peptide. NKLIV... peptide was used at concentrations of 90-448 micromolar. Inhibition of fibrin crosslinking could be detected at 90 micromolar and nearly 100 % inhibition was obtained at 179 micromolar concentrations of the NKLIV... peptide.

EXAMPLE 15

Time Course of DDAVY... Peptide Binding to Preformed Fibrin II

Figure 8:
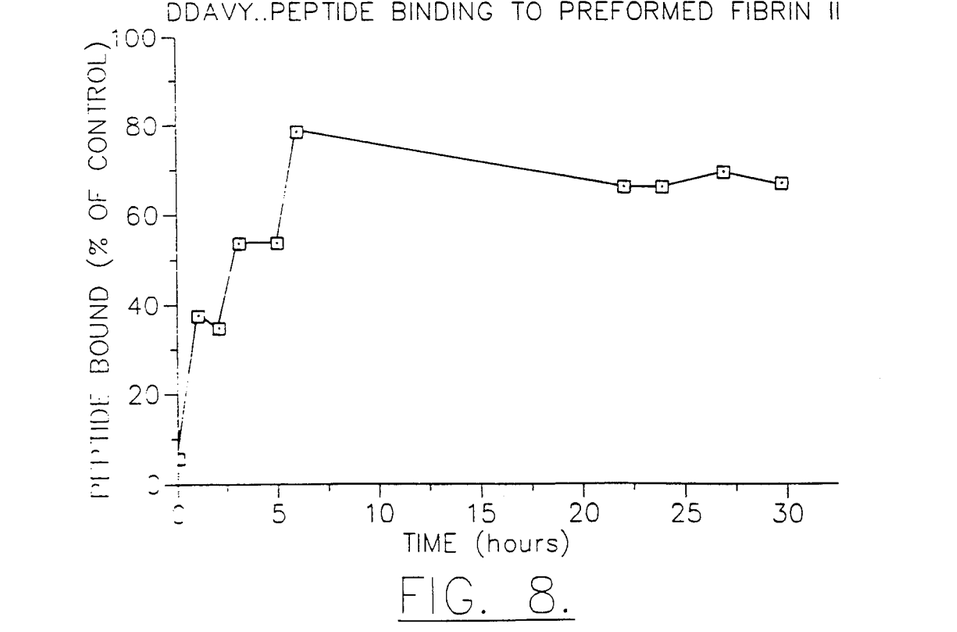
FIG. 8 illustrates the time course of DDAVY... peptide binding to preformed Fibrin II.

This Example illustrates the binding of DDAVY... to preformed fibrin II. Purified human fibrinogen (1.0 mg/mL) was mixed with 10 mM calcium chloride in 0.1M Tris, pH 7.4 containing 0.15M NaCl (Tris-buffered saline, TBS) and clotted by the addition of 10 U/mL thrombin and incubated at 37° C. for 10 minutes. The fibrin was compressed by centrifugation (10,000 rpm, 10 minutes) and washed thrice with TBS (1 mL TBS each time). Then the fibrin pellet was suspended in TBS containing 10 mM calcium chloride, 0.1% Tween-20, 0.1% bovine serum albumin, and radiolabeled DDAVY... peptide (408,000 cpm). The mixture was incubated for different time periods. At the end of each time period, the fibrin was centrifuged down, washed thrice with TBS and the radioactivity bound to the fibrin pellet was measured using a gamma counter. A control binding experiment was conducted simultaneously to determine the amount of peptide bound under optimal conditions (=100% binding) and the binding of the peptide to preformed fibrin II was expressed as the percent of control binding. Data are shown in FIG. 8.

The foregoing examples are illustrative of the present invention, and are not to be construed as limiting thereof. The invention is defined by the following claims, with equivalents of the claims to be included therein.

That which is claimed is:

1. An isolated and purified fibrin-binding peptide selected from the group consisting of:
   (a) isolated peptides consisting essentially of the amino acid sequence of the Blood Coagulation Factor XIIIA fragment which spans amino acids number 72 to 230 shown in FIG. 1C;
   (b) peptides which are fragments of the Factor XIIIA fragment of (a) above, which include in said fragment the sequence (i) NKLIVRRGQSFYVQIDFSRPYDPRRD or (ii) DDAVYLDNEKEREEYVLNDIGVIFYGEVNDIKTRSWSYGQF, and which retain the capability of said fragment of binding to fibrin; and
   (c) peptides which bind to fibrin, which have the amino acid sequence of any of the foregoing peptides, and which have (i) up to about ten additional amino acid residues attached to the N-terminal end, (ii) up to about ten additional amino acid residues attached to the C-terminal end, or (iii) both up to about ten additional amino acid residues attached to the N-terminal end and up to about ten additional amino acid residues attached to the C-terminal end, and which retain the activity of the foregoing peptides of binding to fibrin.

2. An isolated and purified fibrin-binding peptide having the sequence: NKLIVRRGQSFYVQIDFSRPYDPRRDLFRVEYVIGRYPQENKGTYIPVPIVSELQSGKWGAK IVMREDRSVRLSIQSSPKCIVGKFRMYVAVWTPYGVLRTSRNPETDTYILFNPWCEDDAVYL DNEKEREEYVLNDIGVIFYGEVNDIKTRSWSYGQF-R', where R' is selected from the group consisting of —$CONH_2$ and —$NH_2$.

3. A fibrin-binding peptide according to claim 1 having the sequence of: DDAVYLDNEKEREEYVLNDIGVIFYGENVNDIKTRSWSYGQF.

4. An isolated and purified fibrin-binding peptide having the sequence: DDAVYLDNEKEREEYVLNDIGVIFYGEVNDIKTRSWSYGQF-R', where R' is selected from the group consisting of —$CONH_2$ and —$NH_2$.

5. A fibrin-binding peptide according to claim 1 having the sequence of: NKLIVRRGQSFYVQIDFSRPYDPRRD.

6. An isolated and purified fibrin-binding peptide having the sequence: NKLIVRRGQSFYVQIDFSRPYDPRRD-R', where R' is selected from the group consisting of —$CONH_2$ and —$NH_2$.

7. A fibrin-binding peptide according to claim 1 covalently joined to a detectable group.

8. A fibrin-binding peptide according to claim 7, wherein said detectable group is [131]I.

9. A pharmaceutical formulation comprising a fibrin-binding peptide in an amount effective to bind fibrin, in a pharmaceutically acceptable carrier, said fibrin-binding peptide selected from the group consisting of:
(a) isolated peptides consisting essentially of the amino acid sequence of the Blood Coagulation Factor XIIA fragment which spans amino acids number 72 to 230 shown in FIG. 1C;
(b) peptides which are fragments of the FACTOR XIIIA fragment of (a) above, which include in said fragment the sequence (i) NKLIVRRGQSFYVQIDFSRPYDPRRD or (ii) DDAVYLDNEKEREEYVLNDIGVIFYGEVNDIKTRSWSYGQF, and which retain the capability of said fragment of binding to fibrin; and
(c) peptides which bind to fibrin, which have the amino acid sequence of any of the foregoing peptides, and which have (i) up to about ten additional amino acid residues attached to the N-terminal end, (ii) up to about ten additional amino acid residues attached to the C-terminal end, or (iii) both up to about ten additional amino acid residues attached to the N-terminal end and up to about ten additional amino acid residues attached to the C-terminal end, and which retain the activity of the foregoing peptides of binding to fibrin.

10. A pharmaceutical formulation comprising a fibrin-binding peptide in an amount effective to bind fibrin, in a pharmaceutically acceptable carrier, said fibrin-binding peptide having the sequence: NKLVRRGQSFYVQIDFSRPYDPRRDLFRVEYVIGRYPQENKGTYIPVPIVSELQSGKWGAK IVMREDRSVRLSIQSSPKCIVGKFRMYVAVWTPYGVLRTSRNPETDTYILFNPWCEDDAVYL DNEKEREEYVLNDIGVIFYGEVNKIKTRSWSYGQF-R′, where R′ is selected from the group consisting of —CONH₂ and —NH₂.

11. A pharmaceutical formulation according to claim 9, said fibrin-binding peptide having the sequence of: DAVYLDNEKEREEYVLNDIGVIFYGEVNDIKTRSWSYGQF.

12. A pharmaceutical formulation comprising a fibrin-binding peptide in an amount effective to bind fibrin, in a pharmaceutically acceptable carrier, said fibrin-binding peptide having the sequence: DDAVYLDNEKEREEYVLNDIGVIFYGEVNDIKTRSWSYGQF—R′, where R′ is selected from the group consisting of —CONH₂ and —NH₂.

13. A pharmaceutical formulation according to claim 9, said fibrin-binding peptide having the sequence of: NKLIVRRGQSFYVQIDFSRPYDPRRD-R′, where R′ is selected from the group consisting of —CONH₂ and —NH₂.

14. A pharmaceutical formulation comprising a fibrin-binding peptide in an amount effective to bind fibrin, in a pharmaceutically acceptable carrier, said fibrin-binding peptide having the sequence: NKLIVRRGQSFYVQIDFSRPYDPRRD-R′, where R′ is selected from the group consisting of —CONH₂ and —NH₂.

15. An isolated and purified fibrin-binding peptide selected from the group consisting of:
(a) an isolated and purified peptide consisting essentially of the Blood Coagulation Factor XIIIA fragment which spans amino acids number 72 to 230 shown in FIG. 1C;
(b) isolated and purified fragment having the sequence of: DDAVYLDNEKEREEYVLNDIGVIFYGEVNDIKTRSWSYGQF; and
(c) isolated and purified peptides which bind to fibrin, which have the amino acid sequence of any of the foregoing peptides, and which have (i) up to about ten additional amino acid residues attached to the N-terminal end, (ii) up to about ten additional amino acid residues attached to the C-terminal end, or (iii) both up to about ten additional amino acid residues attached to the N-terminal end and up to about ten additional amino acid residues attached to the C-terminal end, and which retain the activity of the foregoing peptides of binding to fibrin.

16. An isolated and purified fibrin-binding peptide selected from the group consisting of:
(a) an isolated and purified peptide consisting essentially of the Blood Coagulation Factor XIIIA fragment which spans amino acids number 72 to 230 shown in FIG. 1C;
(b) isolated and purified fragment having the sequence of: NKLIVRRGQSFYVQIDFSRPYDPRRD; and
(c) isolated and purified peptides which bind to fibrin, which have the amino acid sequence of any of the foregoing peptides, and which have (i) up to about ten additional amino acid residues attached to the N-terminal end, (ii) up to about ten additional amino acid residues attached to the C-terminal end, or (iii) both up to about ten additional amino acid residues attached to the N-terminal end and up to about ten additional amino acid residues attached to the C-terminal end, and which retain the activity of the foregoing peptides of binding to fibrin.

17. A fibrin-binding peptide according to any one of claims 2, 4 or 6, said peptide covalently joined to a detectable group.

18. A fibrin-binding peptide according to claim 17, wherein said detectable group is ¹³¹I.

* * * * *

UNITED STATES PATENT AND TRADEMARK OFFICE
CERTIFICATE OF CORRECTION

PATENT NO. : 5,328,898  Page 1 of 2
DATED : 12 July 1994
INVENTOR(S) : Charles S. Greenberg It is certified that error appears in the above-indentified patent and that said Letters Patent is hereby corrected as shown below:

On title page, item [57] Abstract, line 6, delete the space between EDR and SVR.

Column 10, Claim 2, lines 41 and 43, please delete the spaces.

Column 10, Claim 3, line 49, please correct "NV" to read -- VN --.

Column 11, Claim 9, line 5, please correct "XIIA" to read -- XIIIA --.

Column 11, Claim 10, line 29, please correct "NKLV" to read -- NKLIV --.

Column 11, Claim 10, lines 31 & 33, please delete the spaces.

Column 11, Claim 10, line 34, please correct "KIK" to read -- DIK --.

UNITED STATES PATENT AND TRADEMARK OFFICE
CERTIFICATE OF CORRECTION

PATENT NO. : 5,328,898
DATED : July 12, 1994
INVENTOR(S) : Charles S. Greenberg

It is certified that error appears in the above-indentified patent and that said Letters Patent is hereby corrected as shown below:

Column 11, Claim 11, line 39, please correct "DAV" to read -- DDAV --.

Signed and Sealed this

Twenty-ninth Day of November, 1994

Attest:

BRUCE LEHMAN

*Attesting Officer*    *Commissioner of Patents and Trademarks*